(12) United States Patent
Jerebko et al.

(10) Patent No.: US 9,235,888 B2
(45) Date of Patent: Jan. 12, 2016

(54) IMAGE DATA DETERMINATION METHOD, IMAGE PROCESSING WORKSTATION, TARGET OBJECT DETERMINATION DEVICE, IMAGING DEVICE, AND COMPUTER PROGRAM PRODUCT

(71) Applicant: SIEMENS AKTIENGESELLSCHAFT, Munich (DE)

(72) Inventors: Anna Jerebko, Erlangen (DE); Michael Kelm, Erlangen (DE); Michael Suehling, Erlangen (DE); Michael Wels, Bamberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 325 days.

(21) Appl. No.: 13/780,058

(22) Filed: Feb. 28, 2013

(65) Prior Publication Data
US 2013/0223715 A1    Aug. 29, 2013

(30) Foreign Application Priority Data

Feb. 28, 2012   (EP) .................................... 12157329
Mar. 1, 2012    (EP) .................................... 12001379
Aug. 20, 2012   (EP) .................................... 12181000

(51) Int. Cl.
*G06T 7/00*    (2006.01)
*G06T 3/00*    (2006.01)
(Continued)

(52) U.S. Cl.
CPC ............. *G06T 7/0012* (2013.01); *G06T 3/0093* (2013.01); *A61B 5/0091* (2013.01);
(Continued)

(58) Field of Classification Search
CPC ...... A61B 5/0073; A61B 5/0091; A61B 6/48; A61B 6/502; A61B 6/4417; G06T 7/0012; G06T 7/0014; G06T 2207/10072; G06T 2207/10081; G06T 2207/10084; G06T 2207/30068
See application file for complete search history.

(56) References Cited

U.S. PATENT DOCUMENTS

2003/0007598 A1*   1/2003   Wang et al. ...................... 378/37
2005/0089205 A1*   4/2005   Kapur et al. .................. 382/128
(Continued)

OTHER PUBLICATIONS

Qiu, et al. "Correspondence Recovery in 2-view Mammography." Biomedical Imaging: Nano to Macro, 2004. IEEE International Symposium on (2004): 197-200.*
(Continued)

*Primary Examiner* — Michael A Newman
(74) *Attorney, Agent, or Firm* — Laurence Greenberg; Werner Stemer; Ralph Locher

(57) ABSTRACT

A second form of image data is determined from a first form of image data of an examination object in a radiological imaging system. A set of a defined plurality of input pixels in the image data of the first form is determined. In addition, a set of target form parameters of a target form model with a defined plurality of target form parameters is prognostically determined by way of a data-driven regression method from the plurality of input pixels. The number of target form parameters is smaller than the number of input pixels. The second form of image data is determined from the set of target form parameters. There is also described a method in radiological imaging for determining the geometric position of a number of target objects in a second form of image data and an image processing workstation for determining a second form of image data from a first form of image data as well as an imaging device.

20 Claims, 8 Drawing Sheets

(51) Int. Cl.
*A61B 6/00* (2006.01)
*A61B 5/00* (2006.01)

(52) U.S. Cl.
CPC .............. *A61B 6/4417* (2013.01); *A61B 6/502* (2013.01); *A61B 6/5229* (2013.01); *G06T 2200/04* (2013.01); *G06T 2207/10112* (2013.01); *G06T 2207/30068* (2013.01)

(56) References Cited

U.S. PATENT DOCUMENTS

| | | | |
|---|---|---|---|
| 2007/0038085 A1* | 2/2007 | Zhang et al. | 600/437 |
| 2010/0166147 A1* | 7/2010 | Abenaim | 378/63 |
| 2011/0157154 A1* | 6/2011 | Bernard et al. | 345/419 |
| 2012/0150034 A1* | 6/2012 | DeFreitas et al. | 600/437 |
| 2012/0256920 A1* | 10/2012 | Marshall et al. | 345/420 |

OTHER PUBLICATIONS

Criminisi, et al. "Robust Linear Registration of CT Images Using Random Regression Forests." SPIE Medical Imaging (2011): 1-8.*
Gallego, et al. "Automatic Model-based 3D Segmentation of the Breast in MRI." Proc. of SPIE: Medical Imaging 7962 (2011): 1-8.*
Sanchez, David R. Breast Modelling for Multi-Modal Mammographic Correspondence. Thesis. Universitat De Girona, 2006. N.p.: n.p., n.d.*
Pathmanathan, et al. "Predicting Tumour Location by Modelling the Defomration of the Breast." OxMOS: New Frontiers in the Mathematics of Solids (2008): 1-11.*
Gouveia, et al. "Comparative Evaluation of Regression Methods for 3D-2D Image Registration." ICANN 2012, Part II, LCNS 7553 (2012): 238-45.*
Ardizzone, et al. "Multi-Modal Image Registration Using Fuzzy Kernel Regression." ICIP (2009): 193-96.*
Yan Qui et al: "Correspondence Recovery in 2-View mammography"; Biomedical Imaging: Macro to Nano: IEEE International Symposium on Arlington VA, Piscataway, pp. 197-200, ISBN: 978-0-7803-8389-0, DOI: 10.1109/ISBI.2004.1398508, XP010773831, 2004, US, Apr. 15, 2004.
Stelios K. Kyriacou et al: "Nonlinear Elastic Registration of Brain Images with Tumor Pathology Using a Biomechanical Model"; IEEE Transactions on Medical Imaging, IEEE Service Center, Piscataway, vol. 18, No. 7, pp. 580-592, ISSN: 0278-0062, XP011035875, 1999, US, Jul. 1, 1999.
Yong Zhang et al: "3D Finite Element Modeling of Nonrigid Breast Deformation for Feature Registration in X-ray and MR Images" Applications of Computer Vision, WACV 2007, IEEE Workshop, pp. 38-38, ISBN: 978-0-7695-2794-9, XP031055147, 2007, Feb. 1, 2007.
Lorensen, W., et al., "Marching cubes: A high resolution 3D surface construction algorithm", Proceedings of the 14th Annual International Conference on Computer Graphics and Interactive Techniques, ACM SIGGRAPH Computer Graphics 1987, pp. 163-169, vol. 21, No. 4, New York, New York, USA, URL: http://kucg.korea.ac.kr/seminar/2001/src/PA-01-16.pdf.
Cootes, T., et al., "Active Shape Models—Their Training and Application", Computer Vision and Image Understanding, Jan. 1995, pp. 38-59, vol. 61, No. 1, New York, New York, USA, URL: http://www.wiau.man.ac.uk/~bim/Papers/cviu95.pdf.
Van Schie, G, et al., "Correlating locations in ipsilateral breast tomosynthesis views using an analytical hemispherical compression model", Physics in Medicine and Biology, pp. 4715-4730, Aug. 2011, vol. 56, No. 15, URL: http://iopscience.iop.org/0031-9155/56/15/006/pdf/0031-9155_56_15_006.pdf.
Breiman, L., "Random forests", Oct. 2001, pp. 1-33, URL: http://oz.berkeley.edu/users/breiman/randomforest2001.pdf.
Jerebko, A., et al., "System and method for simulating decompressed view for digital breast tomosynthesis data sets", Invention disclosure, Sep. 2010, Siemens AG.
Liu, D., et al., "Vascular landmark detection in 3D CT data", Medical Imaging 2011: Biomedical Application in Molecular, Structural, and Fumctional Imaging, Proceedings of the Society of Photo-Optical Instrumentation Engineers, Mar. 15, 2011, 7 pages, Lake Buena Vista, FL, USA, URL: http://comaniciu.net/Papers/VascularLandmarks_SPIE11.pdf.

* cited by examiner

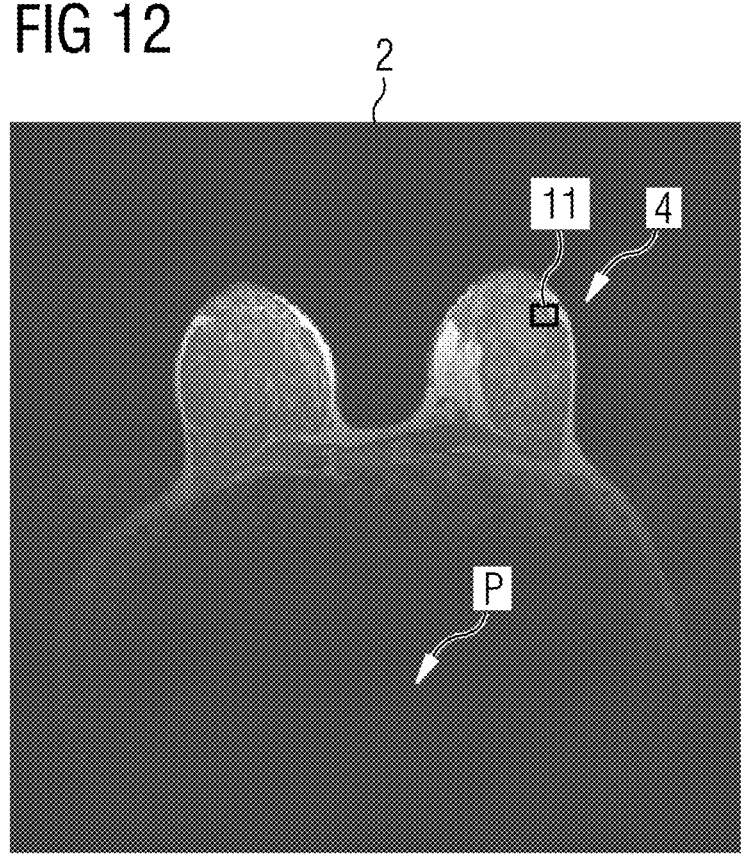

IMAGE DATA DETERMINATION METHOD, IMAGE PROCESSING WORKSTATION, TARGET OBJECT DETERMINATION DEVICE, IMAGING DEVICE, AND COMPUTER PROGRAM PRODUCT

CROSS-REFERENCE TO RELATED APPLICATION

This application claims the priority, under 35 U.S.C. §119, of European patent applications Nos. EP 12 157 329, filed Feb. 28, 2012; EP 12 001 379, filed Mar. 1, 2012; and EP 12 181 000, filed Aug. 20, 2012; the prior applications are herewith incorporated by reference in their entirety.

BACKGROUND OF THE INVENTION

Field of the Invention

The invention relates to a method in radiological imaging for determining a second form of image data from a first form of image data of an examination object. Furthermore the invention relates to an image processing workstation in radiological imaging for determining a second form of image data from a first form of image data as well as an imaging device.

Imaging systems in medical engineering today play an important role in the examination of patients. The images generated by the imaging systems of the internal organs and structures of the patient are used for preventive examinations (screening), for the removal of tissue (biopsy), the diagnosis of causes of illness, for the planning of operations, in the performance of operations or also for the preparation of therapeutic measures. Examples of such imaging systems are ultrasound systems, X-ray equipment, X-ray computed tomography (CT) systems, positron emission tomography (PET) systems, single photon emission tomography (SPECT) systems or magnetic resonance (MR) systems.

The individual imaging systems are distinguished on the one hand by the areas of the patient's body which are to be displayed in the respective application. Thus, devices and systems which are based on X-rays are more suitable for the display of bones and bony structures, while MR systems are more commonly used for the display of muscle or fatty tissue and of the internal organs. On the other hand, the examination times for imaging and the acquisition costs of the imaging system as well as the overall costs of imaging resulting from both play a major role. Accordingly, more cost-effective imaging systems and imaging methods are usually used for routine examinations, such as preventive cancer screening, as these have to be performed on a large number of patients on a regular basis. In contrast more complicated and cost-intensive methods, which usually provide detailed, three-dimensional image data, are often only employed if preventive examinations point to possible diseases or surgical interventions are absolutely essential. On the other hand, the use of the cost-intensive imaging methods for routine examinations is frequently not possible for financial reasons. Furthermore, the expensive, more precise imaging systems are frequently not available at the patient's location or in terms of time.

An additional problem of medical imaging results from the fact that during image acquisition the area of the patient's body concerned must be in a particular position, or by means of additional medical equipment is also put into a particular position or immobilized in a position which is particularly suitable for imaging, in particular to avoid movements of the area of the body during image acquisition, or to improve the image quality by standardizing the acquisition situation and reducing the volume of the body irradiated.

In a subsequent medical intervention on this patient, on the other hand, the part of the patient's body concerned may then be in a sometimes quite different position. In particular the medical intervention will often take place without the aforementioned medical equipment as this might hinder the medical personnel when performing the intervention. However, this now means that the image data of the area of the body does not correspond to the state of the area of the body during the medical intervention, resulting in the medical personnel only being able to use the image data to a limited extent as the basis for performing the intervention, or in there being a risk of the intervention not taking place in the optimum manner as a spatial assignment of the sections for operation in the area of the body concerned may be subject to the aforementioned deviations.

There is therefore a need for methods and devices in radiological imaging with which image data which was generated in a particular form, for example, using a cost-effective imaging system or in a particular positioning of the pertinent area of the body, can be converted into image data of an additional form, for example, into image data which is appropriate for a medical intervention. To solve this problem in medical practice, inter alia, freehand sketches with pre-operative markings are prepared by a radiologist on the basis of the image data, which provide a surgeon with indications as to the positions of the area of the body concerned where medical intervention should take place. However, it is evident that such an approach is prone to error and may therefore be associated with risks for the patient.

Furthermore, first methods are known from G. Schie et al., "Correlating locations in ipsilateral breast tomosynthesis views using an analytical hemispherical compression model", Phys. Med. Biol. 56 (2011), using which certain regions in image data of an area of the body which was compressed by external equipment can be mapped onto image data which was recorded from another imaging angle with different compression. For this purpose, in the case of Schie et al. specific biomechanical assumptions are made and specific biomechanical parameters determined for the area of the body concerned in order to enable the aforementioned imaging. However, as a result this method is limited to the respective area of the body and cannot be transferred to other areas of the body with different biomechanical properties without further ado.

SUMMARY OF THE INVENTION

It is accordingly an object of the invention to provide an image date determination method and device which overcome the above-mentioned disadvantages of the heretofore-known devices and methods of this general type and which provides for a method and a device which determines image data in an appropriate second form from a first form of radiological image data of an examination object and as a result solves the aforementioned problems and avoids the limitations of the known methods.

With the foregoing and other objects in view there is provided, in accordance with the invention, a method in radiological imaging for determining a second form of image data from a first form of image data of an examination object, the method which comprises:

determining a set of a defined plurality of input pixels in the image data of the first form;

prognostically determining a set of target form parameters of a target form model with a defined plurality of target form parameters by way of a data-driven regression method from the plurality of input pixels, wherein the plurality of target form parameters is smaller than the plurality of input pixels; and determining the second form of image data from the set of target form parameters.

With the above and other objects in view there is also provided, in accordance with the invention, an image processing workstation in radiological imaging for determining a second form of image data from a first form of image data of an examination object, the workstation comprising:

an input pixel device configured for determining a set of a defined plurality of input pixels in the image data of the first form;

a prognostic device configured for determining a set of target form parameters of a target form model with a defined plurality of target form parameters by way of a data-driven regression method from the plurality of input pixels, wherein the plurality of target form parameters is smaller than the plurality of input pixels; and an image data determination device configured for determining the second form of image data from the set of target form parameters.

The method according to the invention in radiological imaging for determining a second form of image data from a first form of image data of an examination object consists of a first step in which a set of a defined plurality K of input pixels is determined in the image data of the first form. "Plurality" hereinafter means a positive natural number greater than one. The term "examination object" or "patient" hereinafter means a person receiving medical treatment or an animal receiving medical treatment. Examination objects which exhibit no disease are also included, in other words, also people for whom image data is generated for preventive purposes, e.g. in the case of preventive screening for the prevention of cancer. Subsequently the terms "examination object" and "patient" are used synonymously and without limitation of the invention. In addition, in the invention a distinction is not generally drawn between female and male patients but the male term "patient" is used broadly consistently, even if the method can likewise be employed on female patients.

The image data of the first form can be generated by a measurement or image acquisition with a radiological imaging system. For example, the image data of the first form may involve a two-dimensional image of the area of the body which was recorded with an X-ray device standard in medical practice. Three-dimensional recording methods for the generation of image data of the first form are also conceivable, in other words for example methods involving CT, PET or MR systems. In addition, further manifestations of image data are conceivable, for example three-dimensional image data which is obtained from several two-dimensional image acquisitions with the aid of a so-called 3D tomosynthesis method. Accordingly, the set of input pixels may involve a set of two-dimensional pixels or three-dimensional pixels, for example a vector which consists of a number K of three-dimensional pixels. Hereinafter the terms "set" and "vector" are used synonymously. Symbols for vectors and matrices are shown in bold. The input pixels in the image data of the first form can be determined manually or in an automated fashion or also in an appropriate semi-automatic manner.

In a second step of the method according to the invention, a prognostic determination of a set of target form parameters of a target form model takes place with a defined plurality L of target form parameters by means of a data-driven regression method from the plurality K of input pixels. Advantageously the plurality L of target form parameters is smaller than the plurality K of input pixels. A mathematical model is here described as a target form model which can describe image data of the second form in as compact a manner as possible in order to keep the expense of determining the second form of image data low so that the execution of the method according to the invention is possible in a particularly time-efficient and therefore cost-efficient manner. This is achieved by the target form model reproducing the properties of the image data with a plurality L of target form parameters, wherein the value for L is selected in such a way that the target form parameters represent the image data of the second form sufficiently accurately, but at the same time the value for L is lower than the plurality K of pixels of the input pixels and also lower than a plurality M of pixels which determine the image data of the second form. In particular, an individual target form parameter of the target form model can also describe a plurality of pixels in the image data of the second form, whereby the desired efficiency is produced when determining the image data of the second form.

The plurality L of target form parameters from the plurality K of input pixels is determined in the method according to the invention by means of a regression method. Compared with a purely analytical method, through the use of a regression method it is possible to advantageously ensure that a set of target form parameters can be determined or at least assessed for all conceivable manifestations of the areas of the body of the examination object considered. Through the use of a regression method the method therefore guarantees that image data of the second form can be determined for all examination objects.

In particular, the regression method involves a data-driven regression method, in other words the regression method was derived from existing radiological image data, so-called training image data. Accordingly, no assumptions are made for the regression method about the properties of the examination object. In particular, for determining the regression method it is not necessary to determine biomechanical parameters, such as for example the elasticity of muscle tissue, in advance. The method according to the invention can therefore be used advantageously for many or all areas of the body of the examination object. The training image data forming the basis of the derivation of the regression method typically consists of image data of examination objects which each exist in pairs in the first and in the second form. With the aid of the training image data, the regression method is determined or parameterized and consequently serves in the prognostic determination of image data of the second form for image data which is only available in the first form.

In a third step of the method according to the invention the second form of image data is determined from the set of target form parameters. The target form parameters determined in the second step of the method establish the properties of the target form model so that image data can be easily derived from the now parameterized target form model. For example, two-dimensional image data of the second form can be easily generated from a parameterized three-dimensional target form model by means of averaging with geometric planes. This two-dimensional image data of the second form can then e.g. provide a surgeon with valuable help in identifying critical tissue structures when performing surgical interventions.

The method according to the invention can be advantageously used in a multiplicity of manifestations of radiological image data or a multiplicity of applications in radiological imaging. For example, the image data of the first form could have originated in an image acquisition in which the patient was in a prone position, i.e. lying on his stomach. However, a subsequent medical intervention usually takes place on patients in a supine position. With the aid of the method according to the invention, the image data of the first form in the prone position can now be particularly advantageously converted into image data of the second form in the supine position without additional image acquisitions of the patient in the supine position being necessary. As a result, the time and money spent on radiological imaging are reduced and the radiological burden on the patient, e.g. by X-rays, is reduced. Furthermore, the method according to the invention can be used to convert image data which was generated of patients in a standing position into image data corresponding to a recumbent position. Furthermore, it is possible to convert three-dimensional image data of a patient in the first form, which was generated by means of an X-ray tomosynthesis method, into image data of the second form, which in some cases can be used instead of image data from three-dimensional MR methods, making it possible to dispense with additional time-consuming and cost-intensive MR imaging for this patient.

An image processing workstation according to the invention in radiological imaging for determining a second form of image data from a first form of image data of an examination object consists of an input pixel device for determining a set of a defined plurality K of input pixels in the image data of the first form. In addition, the image processing workstation according to the invention consists of a prognostic device for determining a set of target form parameters of a target form model with a defined plurality L of target form parameters by a data-driven regression method from the plurality K of input pixels, wherein the plurality L of target form parameters is smaller than the plurality K of input pixels. Furthermore, the image processing workstation according to the invention consists of an image data determination device for determining the second form of image data from the set of target form parameters. The input pixel device according to the invention, the prognostic device according to the invention or the image data determination device according to the invention may be partially or wholly accomplished by hardware components, for example using semiconductor chips such as ASICs (Application Specific Integrated Circuits), FPGAs (Field Programmable Gate Arrays), or PLAs (Programmable Logic Arrays).

The dependent claims and the subsequent description contain particularly advantageous developments and embodiments of the invention, wherein in particular the claims of one category can also be developed analogously to the dependent claims of another claim category.

Preferably the method according to the invention is designed in such a way that the set of target form parameters describes a deviation from a standardized geometric target form model. A target form model specific for a particular image acquisition can therefore be described as the total of a standardized geometric target form model and the deviations from this standardized target form model. If, for example, the target form model is described by a set or vector s which contains a plurality N of pixels and if the standardized geometric target form model is described by a set or vector $s_M$, which likewise contains a plurality of pixels N, then the vector s of the target form model can be determined at least approximately as follows:

$$s = s_M + P \cdot y.$$

Here y is the set or vector of target form parameters of the length L and P is a matrix which consists of the basis vectors of the target form model area. In the event that the image data is available in a three-dimensional form, the vector s and the vector $s_M$ each contain N pixels, wherein each pixel i ∈ {1, 2, ..., N} is represented by three numerical values $(x_i, y_i, z_i)$, so that in this case the following applies to the vectors s and $s_M$:

$$s = (x_1, y_1, z_1, x_2, y_2, z_2, \ldots, x_N, y_N, z_N)^T \text{ and}$$

$$s_M = (x_{1M}, y_{1M}, z_{1M}, x_{2M}, y_{2M}, z_{2M}, \ldots, x_{NM}, y_{NM}, z_{NM})^T.$$

The numerical values $x_i$, $y_i$ and $z_i$ are not necessarily coordinates in a Cartesian space. Other spatial representations, such as for example cylindrical or spherical coordinate systems, can also be used within the framework of the method according to the invention. The matrix P from basis vectors can inter alia be determined from existing radiological image data collections or so-called training image data sets which contain the image data of the second form of an examination object. As then the standardized geometric target form model is based on existing training image data sets, it can also be described as a so-called statistical target form model. To determine the matrix P, preferably the method of principal component analysis, PCA, can be employed advantageously.

The standardized geometric target form model is particularly preferably determined by averaging from the given radiological training image data sets. For a given quantity J of training image data $s_t$ where t ∈ {1, 2, ..., J} where:

$$s_t = (x_{1t}, y_{1t}, z_{1t}, x_{2t}, y_{2t}, z_{2t}, \ldots, x_{Nt}, y_{Nt}, z_{Nt})^T$$

the vector $s_M$ of the standardized geometric target form model is therefore:

$$s_M = (s_1 + s_2 + s_3 + \ldots + s_J)/J.$$

In addition to this so-called arithmetic averaging, other notification procedures are also conceivable for the method according to the invention.

Before the average is calculated, all the training image data sets are preferably aligned to some extent in order to obtain a smaller variation in the statistical target form model. In the process, the method of so-called Generalized Procrustes Analysis (GPA) can preferably be applied.

In a preferred embodiment the method according to the invention is characterized in that the determination of a set of a defined plurality K of input pixels in the image data of the first form consists of at least one of the following three method steps. Firstly the first form of the image data is processed by means of a segmentation method step. In other words, essentially, individual areas in the image data are combined to form segments, or are grouped in segments. For image data which is available in two-dimensional form this means that adjacent image data pixels are combined in one segment, insofar as they comply with certain conditions which are also described as homogeneity criteria. Thus, pixels with similar grayscale values, i.e. the grayscale values of which, for example, indicate a similar attenuation of X-rays when passing through an examination object, are combined to form a common segment. Organs, contiguous bone structures or for example the skin surface of the examination object can therefore often be combined to form one segment in the image data by means of such segmentation. A summary corresponding to the pixels can be applied to the so-called voxels in order to segment three-dimensional image data. Particularly preferably segmentation takes place automatically in the process, in other words without manual interventions by an operator, or at least largely automatically with a somewhat smaller number of manual interventions. Threshold value imaging methods ("thresholding") or region growing methods are preferably appropriate for such execution of the segmentation. In the case of the latter, the method is based on one or more starting or seed points, i.e. in the case of two- or three-dimensional image data of seed pixels or seed voxels. Subsequently pixels or voxels adjacent to the seed pixels or seed voxels are always added to the set of seed pixels or seed voxels if they meet a homogeneity criterion.

In addition to the segmentation method step, in the preferred embodiment of the determination of a set of input pixels a number of anatomical landmarks are determined in the first form of the image data. Particularly preferably such a determination takes place using automatic or partially automatic detection methods of machine learning, wherein the landmarks to be detected are particularly preferably represented inside the image data as 3-D hair features, based on the image data of the first form.

In addition, the preferred embodiment of the determination of a set of input pixels is characterized by the determination of a number of interfaces in the segmented image data of the first form, preferably in accordance with a marching cube method, wherein the geometric position of the interfaces is established by the previously determined anatomical landmarks. Subsequently the input pixels are determined in the first form of the image data in such a way that at least some of the input pixels lie on the previously determined interfaces.

Preferably the method according to the invention is characterized by the set of input pixels being determined in such a way that the input pixels are distributed approximately uniformly over a number of interfaces of the area of the body. In particular the input pixels may be arranged in a plurality of groups, wherein the input pixels within a group are at the same physical distance from an anatomical landmark. A group can also consist of only one input pixel.

In a preferred embodiment of the method according to the invention the method is embodied in such a way that it can be applied advantageously to areas of the body of the examination object which occur in pairs in the examination object. This relates to both external pairs of organs of the examination object, such as eyes, ears, hands, arms, legs, feet, breasts, etc. and to internal pairs of organs of the examination object, such as lungs, kidneys, ventricles of the heart, cerebral hemispheres, etc. For this purpose, for the use of the method for the second part of the pair, the method for the first part is used, wherein before the determination of the set of input pixels here the image data of the first form of the second part of the pair is mirrored in a mirror axis and after the determination of the second form of the image data this is again mirrored in a mirror axis. This means that through this embodiment a method according to the invention which was created for the first part of a pair of an area of the body can be applied to the second part of the pair at little expense, without the method for the second part of the pair having to be developed in addition. In particular, advantageously it is not necessary for training image data sets to be available for the second part of the pair of the area of the body of the examination object.

Preferably the method according to the invention can be employed when areas of the body of the examination object are subject to deformation by an external mechanism during the recording of the first form of the image data and the second form of the image data is intended to display the areas of the body without this deformation. Such external mechanisms for the deformation or compression of an area of the body are employed, inter alia, in order to immobilize the area of the body in a particular position during image acquisition or to reduce the volume of the body penetrated by radiation during imaging, or to ensure a defined radiation thickness during imaging. As a result, with the aid of the method according to the invention, image data of an area of the body can be generated in a non-compressed image from its image data in a compressed image.

The method according to the invention is particularly preferred for use on a female breast. In other words, the area of the body subject to deformation consists of a breast. The image data of the first form is then preferably image data which was ascertained by means of a method of breast tomosynthesis. In breast tomosynthesis, in particular digital breast tomosynthesis (DBT), frequently two or more images of a patient are created in various positions. In the process the breast is compressed by a mechanism which consists of plate-like structures during image acquisition, for example by a so-called compression paddle. Imaging positions standard in medical practice are the so-called mediolateral oblique (MLO) position and the so-called cranio-caudal (CC) position. The imaging positions are distinguished by the geometric angle at which the image data is generated, wherein in particular X-ray devices are used for this purpose, in which the X-ray tube can be swiveled, for example at angle increments of +/−25°. With the aid of appropriate reconstruction methods three-dimensional image data can then be generated from two-dimensional image data with different recording angles and then converted into three-dimensional image data in an uncompressed representation with the aid of the method according to the invention. The image data of the second form is then preferably image data of the breast in uncompressed form, e.g. of a standing or lying patient, or in a position lying on her stomach, for example in an MR device. In principle, however, the image data of the second form can also show the breast in a position deformed by external influences, e.g. by a breast coil in the MR device and/or gravitation.

This means that by means of the method according to the invention method it is possible to use image data from relatively inexpensive mammography devices for surgical interventions which take place on the breast in uncompressed form, without the image data being distorted by the compression. In addition to the aforementioned compression of the breast during mammography, the image data of the first form can also originate from image acquisition in which the patient was in a prone position and the breast is deformed by gravitation and/or the breast coil. This applies in particular to so-called face-down MR tomography imaging. In this case too with the aid of the method according to the invention image data of the second form can be determined which corresponds to a non-deformed position, or to image acquisition in a supine position.

Preferably the set of input pixels is determined by the method according to the invention in such a way that the input pixels lie on the surface of the breast and particularly preferably the input pixels are assigned to groups (with one or more input pixels), wherein the input pixels within one group are at approximately the same distance from the papilla of the breast. The method may consist of steps for the at least partially automatic determination of the papilla of the breast.

The prognostic determination of the plurality L of target form parameters from the plurality K of input pixels takes place by means of a regression method in the method according to the invention, i.e. a vector y with a plurality L of target form parameters is determined by the regression method from the vector x with K input pixels. As the number of input pixels is greater than one, preferably so-called multiple regression methods can be employed advantageously as these can process more than one input variable or a multidimensional input variable for determining an output variable. In addition, so-called multivariate regression methods can be employed advantageously as these regression methods are characterized by the fact that they can determine more than one output variable or one multidimensional output variable. A multiple, multivariate regression method therefore provides a function f, for which the following applies:

$$f: X \to Y$$

where:

$$f(x)=y \text{ where } x \in X \text{ and } y \in Y.$$

Here, X represents the K-dimensional real-valued vector space and Y represents the L-dimensional real-valued vector space.

Particularly preferably the regression method is characterized in that it is embodied as multiple, multivariate random forest regression. If this regression is applied to a vector x with K input pixels, then end points or leaves of the regression trees which establish the vector y with its L target form parameters are determined using the regression trees provided in this regression method—starting from the roots of the regression trees. Previously established threshold values or decision-making criteria define the traversing of the regression trees from the roots of the regression trees to the leaves of the regression trees during the execution of the method.

In a particularly preferable embodiment, the data-driven regression method of the novel method is characterized in that the regression method is automatically derived from radiological training image data sets using methods of machine learning.

An additional preferred embodiment of the method according to the invention is characterized in that the plurality L of target form parameters is significantly smaller than the plurality K of input pixels. As a result the expense of determining the parameters of the target form parameter is significantly reduced in an advantageous manner so that the method according to the invention can be executed efficiently and accordingly the image data of the second form is available without relatively long waiting times. However, in order for the particular image data of the second form to be of good quality in spite of the relatively small number of target form parameters, the target form parameters are preferably selected in such a way that the cumulative variance of the target form model reflects a cumulative variance of radiological training image data sets for the most part, preferably by at least 80%. This can, for example, be achieved by the target form parameters being determined in such a way that they reflect the significant deviations or directions of deviation from a standardized geometric target form model, while the insignificant deviations from the standardized geometric target form model are not reflected by the target form parameters.

The method according to the invention can preferably be used within the framework of a position determination method of radiological imaging, in which the geometric position of a number of target objects in a second form of image data is determined from the geometric position of the target objects in a first form of image data of an area of the body of an examination object. "Number" is hereinafter taken to mean a positive natural number greater than zero. A target object generally means a region in the area of the body of the examination object considered which is of particular interest for the respective medical examination. Both target objects as they occur in healthy patients as well as target objects which point to a disease may be involved here. For example, the target objects may consist of lesions, tissue changes, bone changes or fractures, internal bleeding, benign and malignant tumors or calcification.

A first step in this position determination method consists of the determination of the second form of image data from the first form of image data of the examination object, preferably using steps in accordance with the method according to the invention. Alternatively, however, other methods can also be used for this step. In an additional step a number of interfaces of the area of the body in the first form and in the second form of the image data are determined. Such interfaces may be any anatomical interfaces inside the examination object or be at the external boundary of the examination object. These include, for example, the surface of the skin, the top of the skull, the diaphragm, the intestinal wall or the stomach wall. A further step of the position determination method consists of the determination of a plurality of anatomical landmarks in the image data of the first form and of the second form. In general anatomical landmarks are anatomical conditions pertaining to the examination object which have special properties or which are easily identifiable. Examples of anatomical landmarks are the corner of the eye, the apex of the nose, the nipple (papilla), a particular vertebrae of the vertebral column, or the anterior commissure (AC), and posterior commissure (PC), of the brain.

In a further step of the position determination method, a geometric curve is determined in such a way that the curve runs at least approximately in the interface and through the plurality of anatomical landmarks. This determination takes place both in the image data of the first form as well as in the image data of the second form. Subsequently curve points are determined in the geometric curves, wherein preferably the curve points are uniformly distributed between pairs of anatomical landmarks and are therefore arranged equidistantly, for example.

In a further step of the position determination method a plurality of contours is determined in the interfaces of the first and second form of image data, wherein the determination of the contours is selected in such a way that in each case one contour runs through a curve point. Preferably the contours are so-called splines. In the mathematical sense, a spline is a curve which runs through a certain number of points and connects these to each other "smoothly." Splines are generally known to the expert in the field of mechanical engineering. They are used there to describe geometric shapes, for example, of ships' hulls or bodywork parts in automotive engineering.

The geometric position of the aforementioned target objects in the second form of the image data is described by means of interpolation in a further step of the position determination method as a function of the contours in the second form of image data, preferably by means of thin plate spline interpolation (TPS interpolation), between the contour points of the first form of the image data and of the second form of the image data. According to the invention, the thin plate splines are used advantageously to describe the deformation of the volume when converting the image data from one form into the other based on the aforementioned anatomical interfaces.

The position determination method makes it possible to advantageously display medically relevant target objects in image data in such a way that in medical interventions, for example, preventive or therapeutic biopsies, these can be easily identified and located in image data with good geometric accuracy by medical personnel. This applies in particular when the image data of the first form was included in a position of the examination object or the area of the body concerned other than the position in which the biopsy is performed. For example, if critical target objects are identified by the medical personnel during image acquisition in a standing position of the examination object, then these target objects can then be displayed in image data of a second form which corresponds to a different position of the examination object using the method according to the invention.

To execute the position determination method a target object determination device may be used which has an interface arrangement for the acceptance of image data of the examination object in a first form and of data concerning target objects in the first form of the image data and for the acceptance of image data in a second form. This target object determination device must then be embodied to perform the following steps:

- determining a number of interfaces of the area of the body in of the first form of the image data and in the second form of the image data,
- determining a plurality of anatomical landmarks in the image data of the first form and in the image data of the second form,
- determining a geometric curve in of the first form of the image data and in the second form of the image data, wherein the curves each run at least approximately in the interface and through the plurality of anatomical landmarks,
- determining curve points in the geometric curves,
- determining a plurality of contours in the interface of the first form of the image data and in the interface of the second form of the image data,
- describing the geometric position of the target objects in the image data of the first form as a function of the contours of the first form of the image data, and
- determining the geometric position of the target objects in the image data of the second form as a function of the contours of the second form of the image data, using interpolation between contours of the first form of the image data and contours of the second form of the image data.

The target object determination device may also be integrated into the image processing workstation according to the invention in such a way that it uses the interim results generated in various interim steps of the method according to the invention such as e.g. anatomical landmarks or interfaces in target object determination.

An imaging device according to the invention, for example an ultrasound system, an X-ray device, a mammography system, an X-ray computed tomography (CT) system, a positron emission tomography (PET) system, a single photon emission tomography (SPECT) system or magnetic resonance (MR) system is characterized by an image processing workstation according to the invention and/or target object determination device.

Technical implementation of the method according to the invention may take place in a wide variety of ways. In particular, it is conceivable that implementation takes place at least partially with the aid of electric circuits such as ASICs (Application Specific Integrated Circuits), FPGAs (Field Programmable Gate Arrays), or PLAs (Programmable Logic Arrays). Furthermore, a computer program product which can be directly loaded into the memory of a programmable imaging device and/or image processing workstation can execute the method according to the invention at least partially by means of program codes when the computer program product is executed in the imaging device or image processing workstation.

Other features which are considered as characteristic for the invention are set forth in the appended claims.

Although the invention is illustrated and described herein as embodied in an image data determination method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 12 an example with image data of the second form and a target object determined by the method according to the invention.

DETAILED DESCRIPTION OF THE INVENTION

The invention is described below, without restriction of generality, in an application on a female breast. The image data of the first form comprises image data from digital breast tomosynthesis (DBT) which as is customary was reconstructed from recordings in the mediolateral oblique (MLO) position and the cranio-caudal (CC) position respectively, and which is therefore based on image data of the correspondingly compressed breast or contains this image data. The image data of the second form involves image data of the uncompressed breast.

Figure 1:
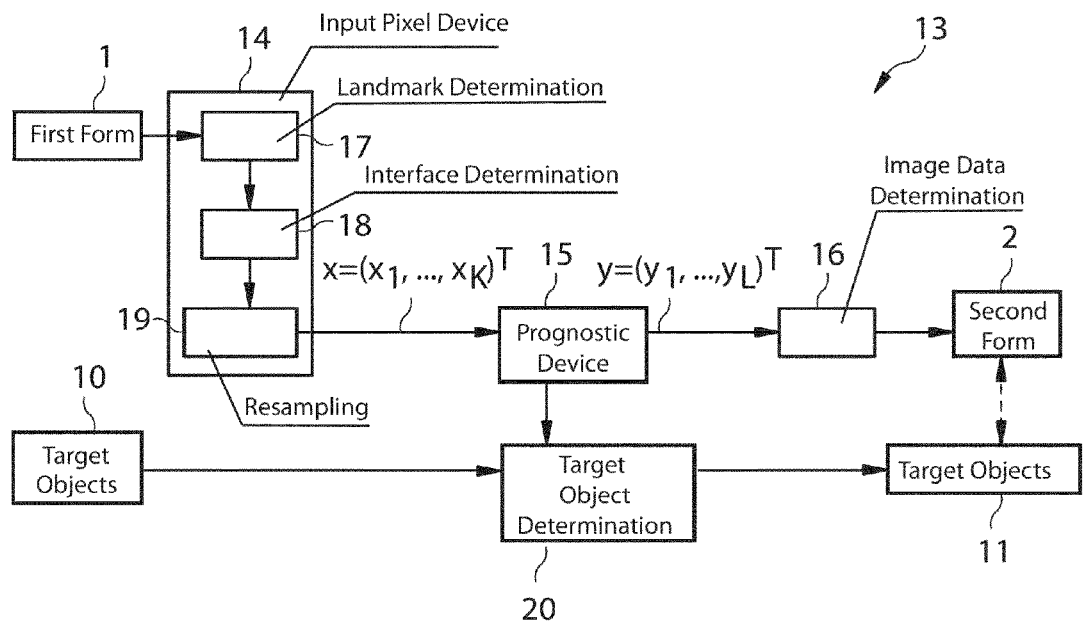
FIG. 1 is a schematic diagram of an image processing workstation according to the invention.

Referring now to the figures of the drawing in detail and first, particularly, to FIG. 1 thereof, there is shown an image processing workstation 13 according to the invention, which determines image data of the second form 2 from image data of the first form 1 of an examination object P. The image processing workstation 13 has an input pixel device 14 for determining a set x of a defined plurality of input pixels $x_1, \ldots, x_K$. The input pixel device 14 consists of a landmark determination device 17 for determining a plurality of anatomical landmarks in the image data of the first form 1. The landmark determination device 17 may likewise have appropriate segmentation devices for the segmentation of the image data of the first form 1 at its disposal. In addition, the input pixel device 14 comprises an interface determination device 18 which determines interfaces such as the surface of the skin, the top of the skull, the diaphragm, the intestinal wall or the stomach wall in the, if need be, already segmented image data of the first form 1. Furthermore the input pixel device 14 comprises a resampling facility 19, which determines input pixels $x_1, \ldots, x_K$ and distributes these in a predefined manner in the image data of the first form 1 using resampling methods, for example so that the distribution of the input pixels $x_1, \ldots, x_K$ is approximately uniform in one of the interfaces 9. In addition, the image processing workstation 13 consists of a prognostic device 15 which determines a set of target form parameters y of a target form model with a defined plurality L of target form parameters $y_1, \ldots, y_L$ by means of a data-driven regression method from the input pixels $x_1, \ldots, x_K$, wherein according to the invention the plurality L of target form parameters $y_1, \ldots, y_L$ is smaller than the plurality K of input pixels $x_1, \ldots, x_K$. From the target form parameters $y_1, \ldots, y_L$ determined in this way an image data determination device 16 determines the second form of image data 2. In addition an image processing workstation 13 according to the invention may consist of devices with which target objects 11 are determined in the image data of the second form 2. In this regard FIG. 1 shows a target object determination device 20 which is part of the image processing workstation 13 here and is embodied in such a way that it determines target objects 11 in the image data of the second form 2 from target objects 10 in the image data of the first form 1 using the method according to the invention. For this purpose it accepts e.g. (as shown symbolically in FIG. 1) the necessary data, in particular the image data of the first form 1 and of the second form 2 from the prognostic device 15 or from the devices associated with the prognostic device 15.

Figure 2:
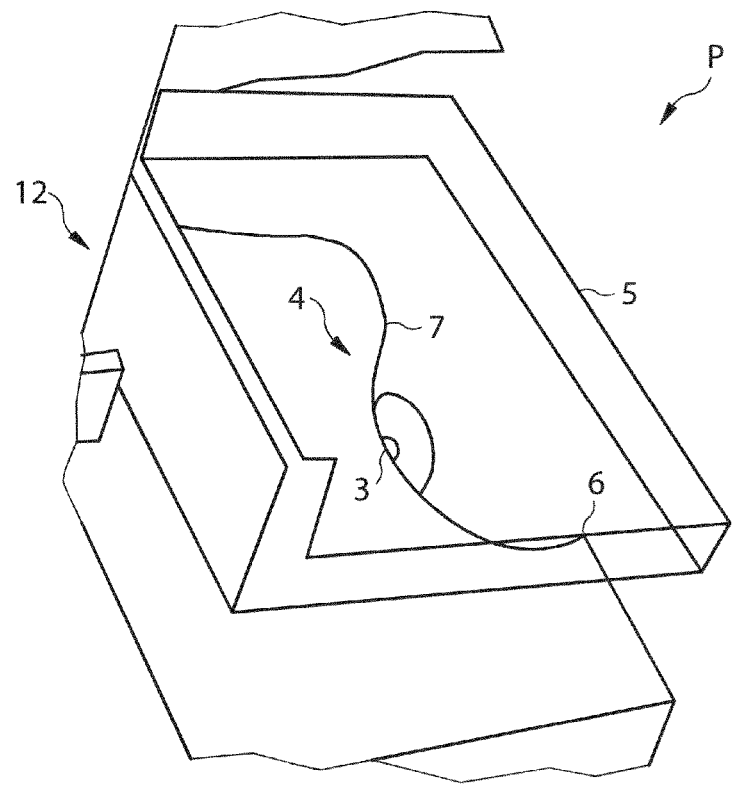
FIG. 2 is a partial perspective view of a mammography device.

FIG. 2 represents a mammography device 12 as is standard in medical practice for the generation of image data of a breast 4 of a patient P. In particular such mammography devices 12 are used to generate DBT image data. The breast 4 is immobilized and compressed by means of a mechanical mechanism, the so-called paddle 5. In an exemplary manner FIG. 2 shows a positioning of the patient P in the MLO position. In addition the papilla 3, the top of the breast 7 and the inframammary fold 6, which in medical practice is also called the inframammary crease or line, are shown.

Figure 3:
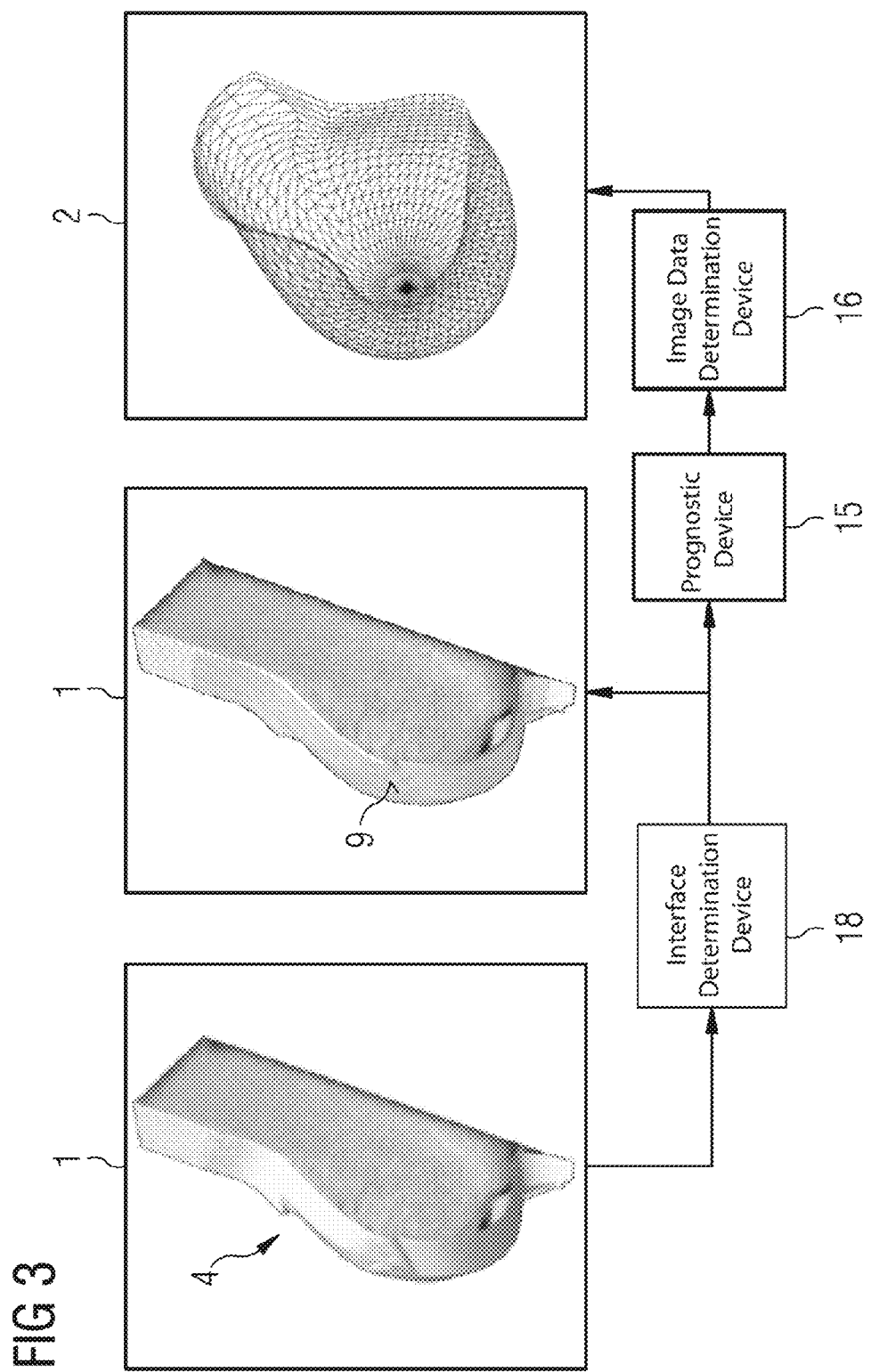
FIG. 3 is an illustration of exemplary image data of the first and the second form for the method according to the invention.

FIG. 3 shows image data of the first form 1 and the corresponding image data of the second form 2 of an exemplary nature for the method according to the invention. In particular FIG. 3 shows how in the image data of the first form 1, which was already segmented, an interface 9 is determined using an interface determination device 18 as an interim step of the method. The interface 9 in this example involves the surface of the skin of a breast 4. In addition FIG. 3 shows the image data of the second form 2, which was determined using a prognostic device 15 and an image data determination device 16. In particular FIG. 3 shows how image data of the second form 2 in a non-compressed manner can be advantageously predicted by the invention from image data of the first form 1, which shows the breast 4 in compressed form, without further image acquisition.

Figure 4:
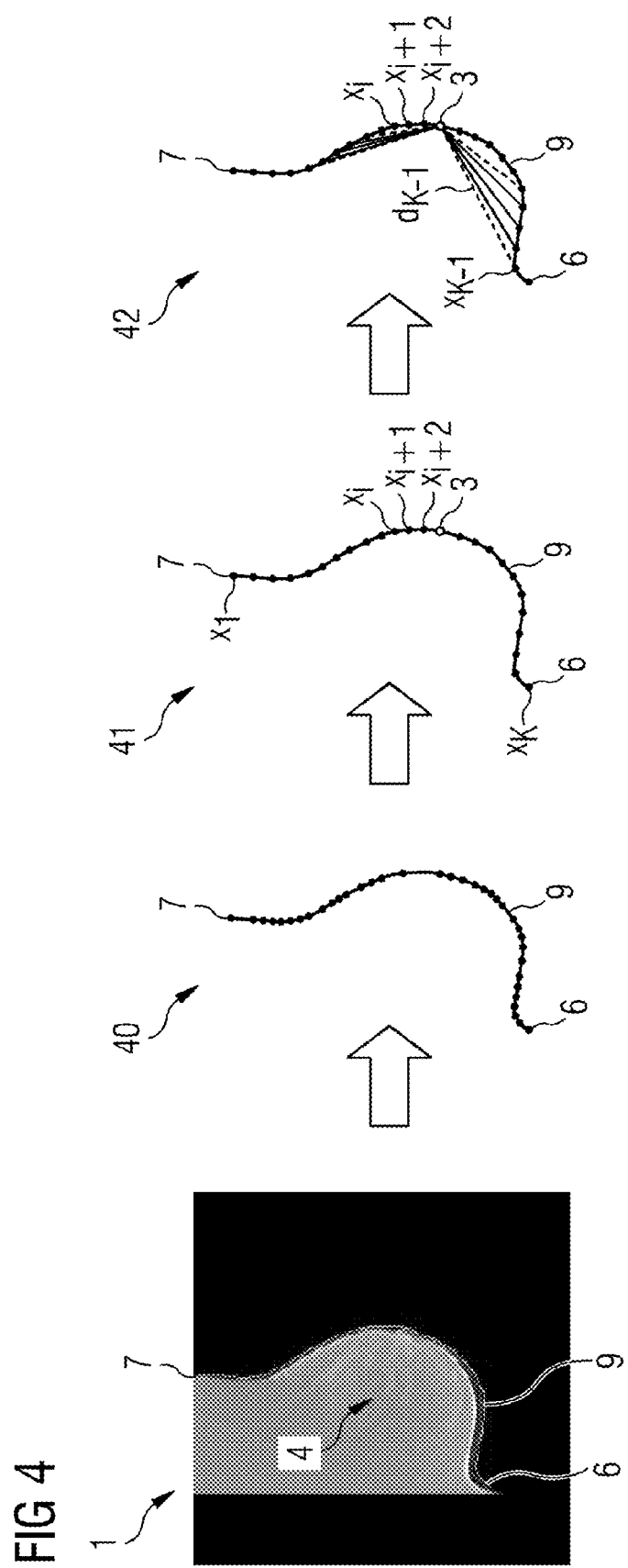
FIG. 4 is an exemplary sequence of the method according to the invention for determining input pixels.

FIG. 4 shows the method steps according to the invention for determining the set of input pixels $x_1, \ldots, x_K$ in the image data of the first form 1 using the example of image data of a breast 4. For this purpose in the image data of the first form 1 firstly characteristic anatomical landmarks of the area of the body of the patient P considered are determined. In the example selected for FIG. 4 the inframammary fold 6 and the top of the breast 7 are identified in the image data of the first form 1. This identification can take place automatically or also with the manual support of the medical personnel. Subsequently in a first method step 40 for determining the input pixels $x_1, \ldots, x_K$ an interface 9 is extracted which runs through the inframammary fold 6 and the top of the breast 7 and which is defined by a number of pixels. In a further method step 41 the number of pixels is modified by removing existing pixels or generating additional ones in such a way that their number corresponds to the defined plurality K. Furthermore, the input pixels are positioned on the interface 9 by means of resampling methods, for example in such a way that they are uniformly distributed on the interface 9. In particular in this method step 41 additional landmarks can be determined, for example the papilla 3. The uniform distribution of the pixels may be selected in such a way that the pixels are arranged equidistantly between the landmarks, for example therefore equidistantly between the papilla 3 and the inframammary fold 6, or equidistantly between the papilla 3 and the top of the breast 7. This results in the input pixels $x_1, \ldots, x_K$. Furthermore in a method step 42 distance vectors $d_1, \ldots, d_K$ are calculated between a number of landmarks and the input pixels $x_1, \ldots, x_K$. The distance vectors $d_1, \ldots, d_K$ are suitable as input variables for the prognostic, data-driven regression method for determining the defined plurality L of target form parameters $y_1, \ldots, y_L$.

In the example shown in FIG. 4 and other figures it goes without saying that the methods and devices according to the invention are naturally also suitable for three-dimensional image data of the first form 1 and three-dimensional image data of the second form 2 and can be used advantageously even if a two-dimensional image was selected here for reasons of clarity. In particular in the figures the interfaces 9 and additional planes are shown as lines on account of the image selected here—but without restricting the application of the invention.

Figure 5:
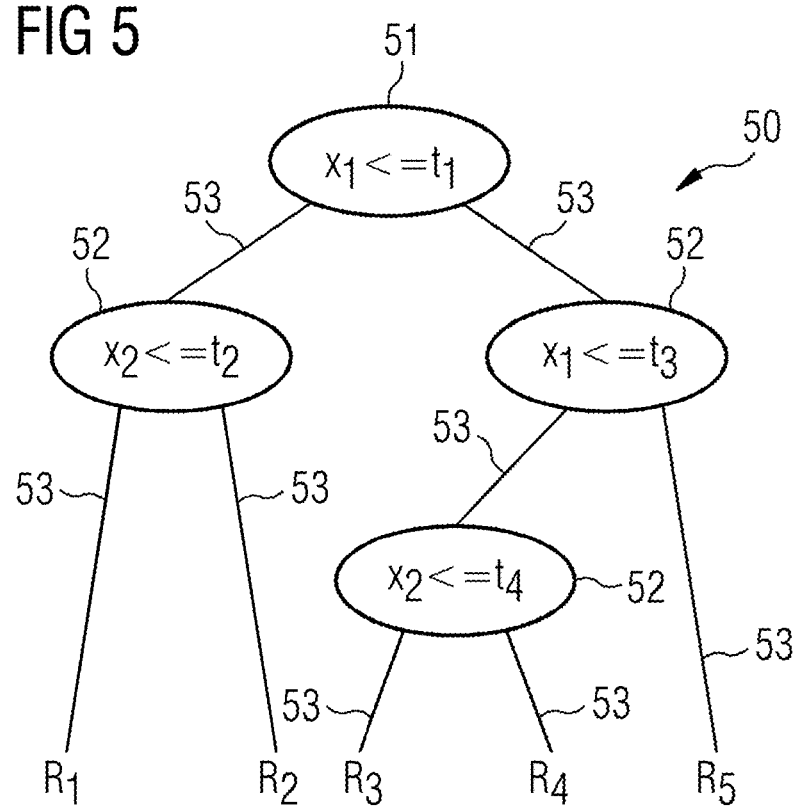
FIG. 5 is an example of a regression tree of an exemplary regression method.

FIG. 5 shows a regression tree 50 of a simple, exemplary regression method with two input variables $x_1$ and $x_2$ and two target variables $y_1$ and $y_2$. The regression methods used in the invention, in particular the multiple, multivariate regression methods, are explained in more detail as a result. A regression tree 50 consists here of a root 51, several nodes 52, several branches 53 and the leaves $R_1, R_2, R_3, R_4, R_5$. During the execution of the regression method a decision is taken at the nodes 52 on the basis of the threshold values $t_1, t_2, t_3, t_4$ as to which additional branches 53 of the regression tree 50 are traversed from the root 51 to the leaves $R_1, R_2, R_3, R_4, R_5$. The decisions depend on several input variables $x_1$ and $x_2$, so that this involves a regression tree 50 for a multiple regression method. At the end of the regression method after traversing the regression tree 50 as a function of the input variable $x_1, x_2$ one of the regions $R_1, R_2, R_3, R_4$ or $R_5$ is determined. On the basis of these regions $R_1, R_2, R_3, R_4, R_5$ values can be determined for the target variables $y_1, y_2$, which is clear in the overall view with FIG. 6 and FIG. 7. As the regression method illustrated here has more than one target variable $y_1, y_2$, it is a multivariate regression method.

Figure 6:
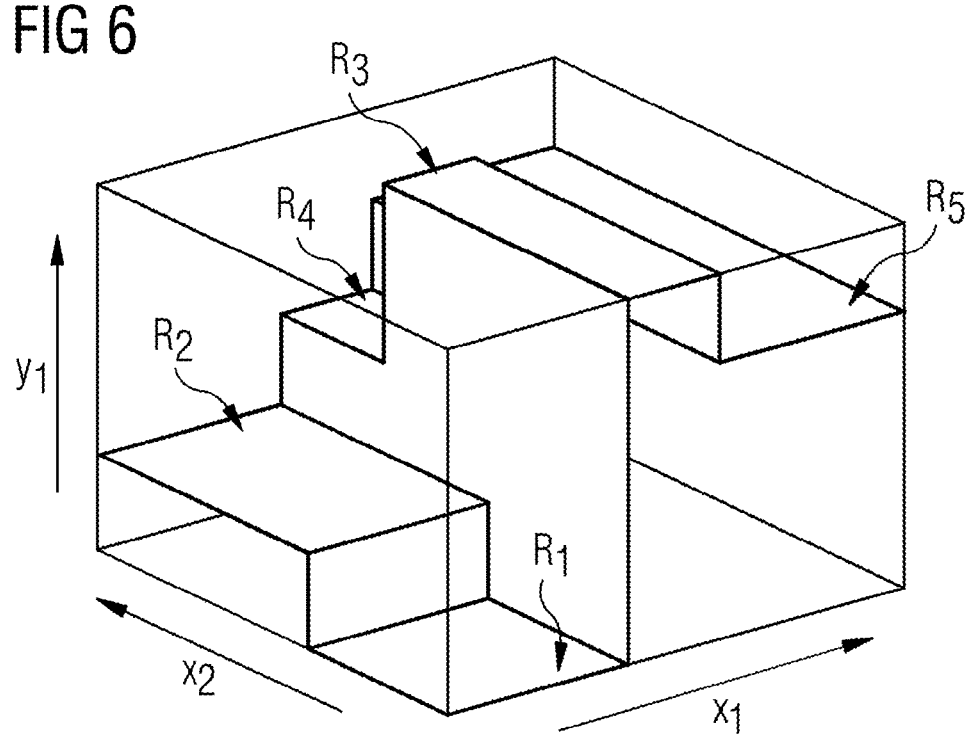
FIG. 6 is an example of the determination of a first target variable of the exemplary regression method.

FIG. 6 shows an example of the determination of a first target variable $y_1$ of the exemplary regression method. As a function of the values of the input variables $x_1$ and $x_2$ a region $R_1, R_2, R_3, R_4, R_5$ is determined which then establishes the value of the target variable $y_1$.

Figure 7:
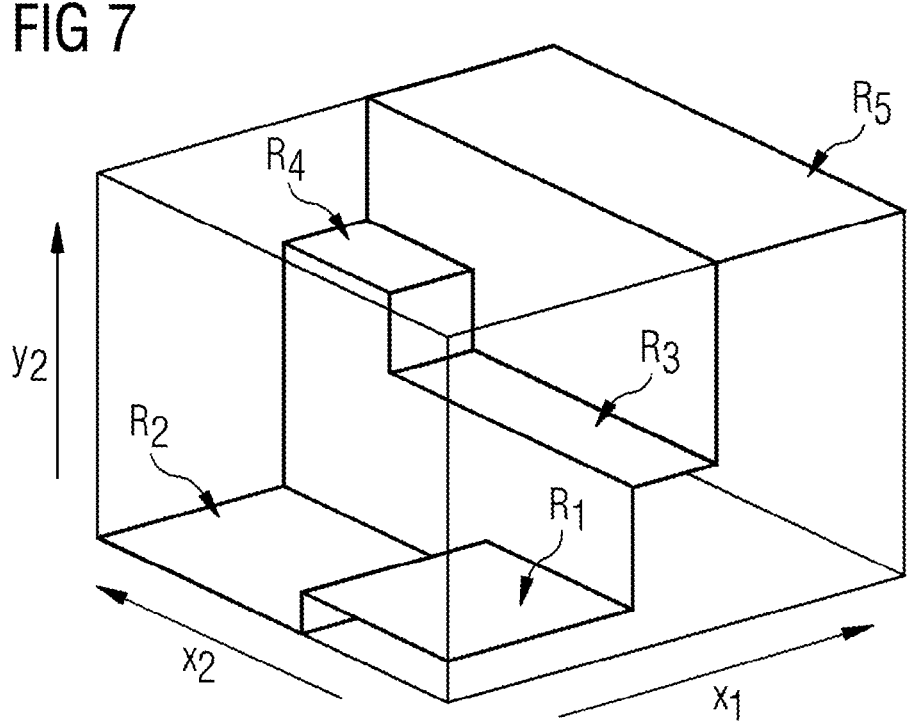
FIG. 7 is an example of the determination of a second target variable of the exemplary regression method.

FIG. 7 shows the establishment of the value for the target variable $y_2$ in corresponding manner for the regression method.

Figure 8:
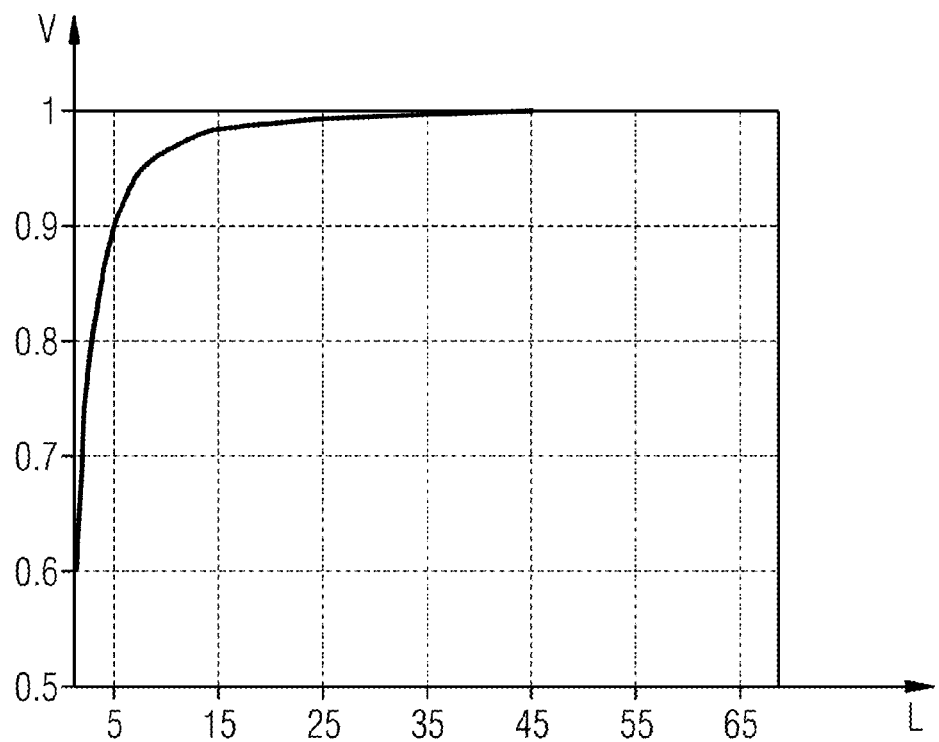
FIG. 8 is an example of the cumulative variance of the target form model as a function of the plurality of target form parameters.

FIG. 8 shows an example of the cumulative variance V of the target form model as a function of the plurality L of target form parameters $y_1, \ldots, y_L$. It is clear that a relatively small plurality L of target form parameters $y_1, \ldots, y_L$ is already sufficient to map the cumulative variance of the image data of the second form 2. For example, according to FIG. 8 90% of the cumulative variance of the image data of the second form 2 is already mapped by only five target form parameters $y_1, \ldots, y_5$. This means that the method according to the invention can be performed very efficiently with a small plurality L of target form parameters $y_1, \ldots, y_5$, without the quality of the prognosis from image data of the second form 2 being significantly impaired as a result.

Figure 9:
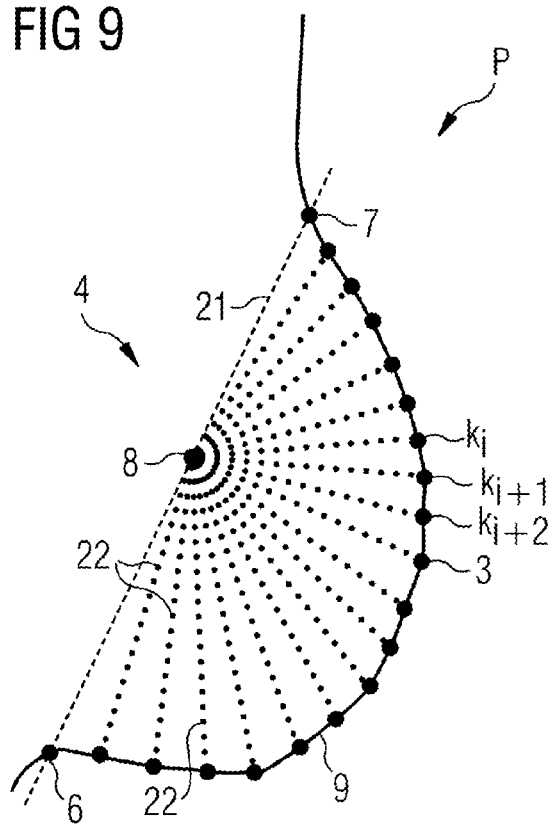
FIG. 9 is an exemplary application of the method according to the invention for determining curve points.

FIG. 9 provides an exemplary application of the method according to the invention for determining the curve points $k_1, \ldots, k_K$ and the contours in the image data of the first form 1 and of the second form 2 of a breast 4 of a patient P. For this purpose firstly characteristic anatomical landmarks such as the papilla 3, the inframammary fold 6 and the top of the breast 7 are determined in the image data of the first form 1 and of the second form 2. Then a determination of an interface 9 which runs through the determined landmarks 3, 6, 7 takes place. In addition a curve k is determined in each case, which is established by the curve points $k_1, \ldots, k_K$, and runs approximately in the interface 9 as well as through the anatomical landmarks 3, 6, 7. The curve points $k_1, \ldots, k_K$ are preferably established in such a way that they are distributed approximately uniformly on the curve. In addition, the breast plane 21 is determined, which is vertical to the MLO plane and which runs through the points established by the inframammary fold 6 and the top of the breast 7. Then a projection of the papilla 3 onto the breast plane 21 takes place, by means of which a projection point 8 of the papilla 3 is produced. In an additional step, planes 22 which are produced by rotating the breast plane 21 around the projection point 8 are established in such a way that they run through the curve points $k_1, \ldots, k_K$.

Figure 10:
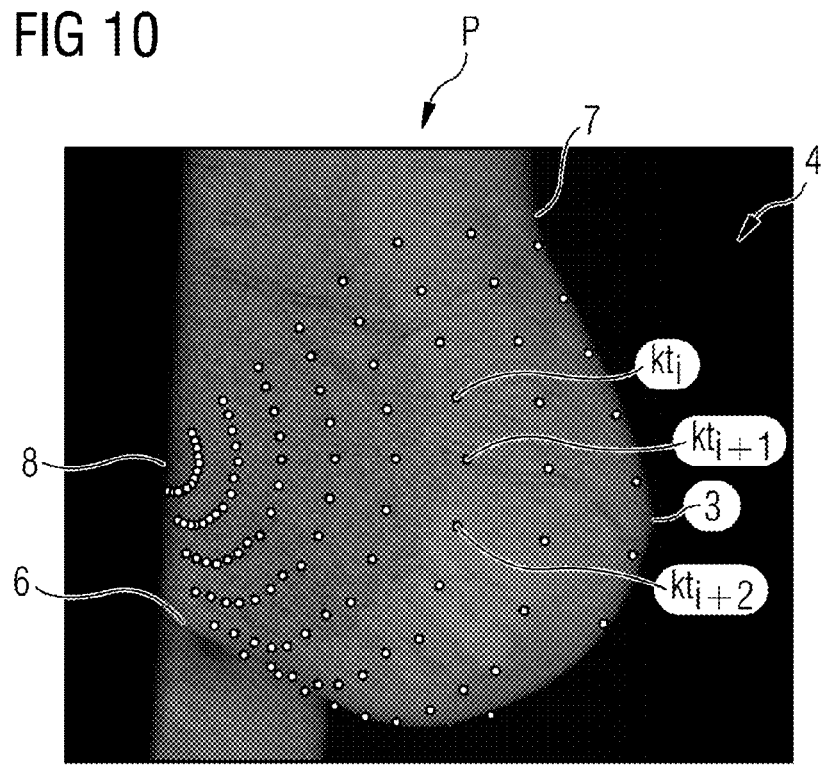
FIG. 10 is an example with image data of the first form and the associated contour points.
Figure 11:
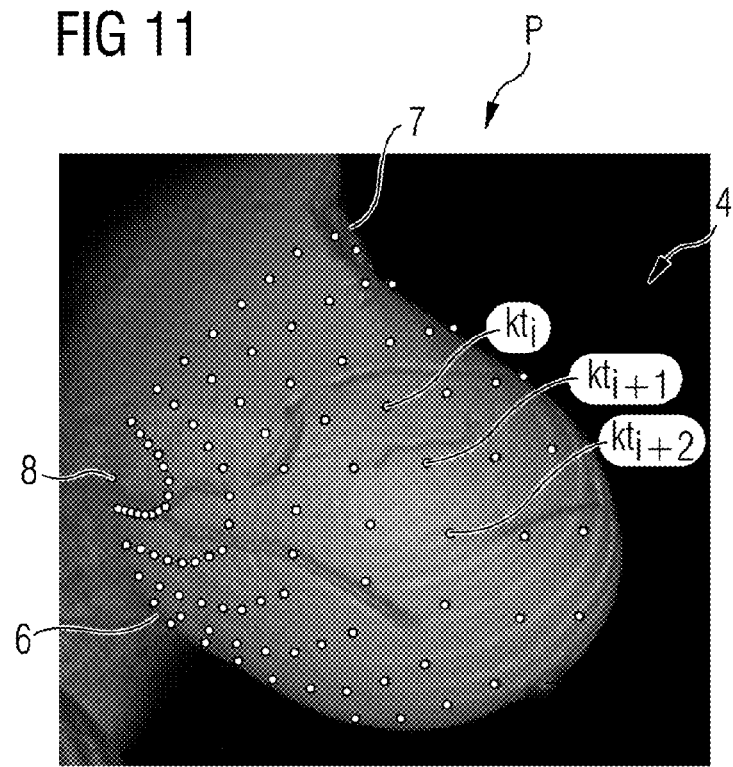
FIG. 11 is an example with image data of the second form and the associated contour points.

With the aid of the curve points $k_1, \ldots, k_K$ or of the rotated breast planes 22 determined in this way, contour points $kt_1, \ldots, kt_K$ can be determined in the interface 9 of the image data of the first form 1 by means of section formation between the rotated breast planes 22 and the interface 9. This is shown in exemplary fashion in FIG. 10. Correspondingly FIG. 11 shows the contour points $kt_1, \ldots, kt_K$ in the interface 9 of the image data of the second form 2, which were determined in turn by means of section formation between the rotated breast planes 22 and the interface 9. The contour points $kt_1, \ldots, kt_K$ in the interface 9 of the image data of the first form 1 and the image data of the second form 2 can now be used to describe target objects 10, 11 which are inside the breast 4. This can, for example, be achieved by a spatial thin plate spline interpolation between the contour points (i.e. any points on the contour). With the corresponding application of thin plate spline interpolation in the description of the target objects 10 in the image data of the first form 1 to the contours of the image data of the second form 2, it is possible to determine the position of the target objects 11 in the image data of the second form 2.

FIG. 12 shows a target object 11 in the image data of the second form 2 determined by the method according to the invention. As can be seen from FIG. 12, the position of the particular target object 12 only deviates approximately 10 mm from the lesion which is discernible as altered coloring in FIG. 12. Such a deviation confirms the suitability of the automatically executable method according to the invention for medical practice.

In conclusion it is once again pointed out that the aforementioned detailed descriptions of methods and image processing workstations are only exemplary embodiments which can be modified by those of skill in the pertinent art in a wide variety of ways without departing from the scope of the invention. In particular, the methods according to the invention for instance may not only be used advantageously for the area of the body of the breast but also for the radiological imaging of other areas of the body. For the sake of completeness it is also pointed out that the use of the indefinite article "a" or "an" does not preclude the possibility of the features concerned being present in multiple instances.

The invention claimed is:

1. A method in radiological imaging, the method comprising the following steps:
   determining a geometric position of a number of target objects in a second form of image data from a geometric position of the target objects in a first form of image data of an area of the body of an examination object, by:
      determining a set of a defined plurality of input pixels in the image data of the first form;
      prognostically determining a set of target form parameters of a target form model with a defined plurality of target form parameters by way of a data-driven regression method from the plurality of input pixels, wherein the plurality of target form parameters is smaller than the plurality of input pixels; and
      determining the second form of image data from the set of target form parameters;
   determining a number of interfaces of the area of the body in the first form of the image data and in the second form of the image data;
   determining a plurality of anatomical landmarks in the image data of the first form and in the image data of the second form;
   determining a geometric curve in the first form of the image data and in the second form of the image data, wherein each of the curves run at least approximately in the interface and through the plurality of anatomical landmarks;
   determining curve points in the geometric curves;
   determining a plurality of contours in the interface of the first form of the image data and in the interface of the second form of the image data;
   describing a geometric position of the target objects in the image data of the first form as a function of the contours of the first form of the image data; and
   determining the geometric position of the target objects in the image data of the second form as a function of the contours of the second form of the image data, by interpolating between contours of the first form of the image data and contours of the second form of the image data.

2. The method according to claim 1, wherein the set of target form parameters describes a deviation from a standardized geometric target form model.

3. The method according to claim 2, wherein the standardized geometric target form model is determined from given radiological training image data sets.

4. The method according to claim 3, wherein the standardized geometric target form model is determined by way of averaging.

5. The method according to claim 1, wherein the step of determining the set of the defined plurality of input pixels in the image data of the first form comprises the following method steps:
   segmenting the first form of the image data;
   determining a number of anatomical landmarks in the first form of the image data;
   determining a number of interfaces in the segmented image data of the first form, wherein the geometric position of the interfaces is established by way of the anatomical landmarks; and
   determining the input pixels so that at least some of the input pixels lie on the interfaces.

6. The method according to claim 5, wherein:
the step of segmenting the first form of the image data comprises automatic segmentation optionally characterized by thresholding and/or regional growing method steps;
the step of determining a number of anatomical landmarks in the first form of the image data comprises implementing automatic methods of machine learning;
the step of determining a number of interfaces in the segmented image data of the first form comprises implementing a marching cube method.

7. The method according to claim 1, wherein, for those areas of the body of the examination object which occur in pairs on the examination object, applying the method applied to the first part of the pair to the second part of the pair, wherein the image data of the first form of the second part of the pair are mirrored in a mirror axis before determining the set of input pixels and again mirroring the set of input pixels in a mirror axis after the step of determining the second form of the image data.

8. The method according to claim 1, wherein areas of the body of the examination object are subject to deformation by an external mechanism during an acquisition of the first form of image data and the second form of image data represent those areas of the body without the deformation.

9. The method according to claim 8, wherein the image data of the first form are ascertained by way of a breast tomosynthesis process and the area of the body subject to deformation consists of a breast.

10. The method according to claim 9, wherein the set of input pixels is determined such that the pixels lie on a surface of the breast.

11. The method according to claim 10, wherein the set of input pixels are assigned to groups, with the input pixels of a given group being located approximately equidistant from the papilla of the breast.

12. The method according to claim 1, wherein the regression method is implemented as multiple, multivariate Random-Forest-Regression.

13. The method according to claim 1, wherein the regression method is automatically derived from radiological training image data sets using methods of machine learning.

14. The method according to claim 1, wherein the plurality of target form parameters is significantly smaller than the plurality of input pixels, wherein the target form parameters are selected in such a way that a cumulative variance of the target form model reflects a cumulative variance of most of the radiological training image data sets.

15. The method according to claim 14, wherein the cumulative variance of the target form model reflects the cumulative variance of radiological training image data sets by at least 80%.

16. A method in radiological imaging for determining a geometric position of a number of target objects in a second form of image data from a geometric position of the target objects in a first form of image data of an area of the body of an examination object, the method comprising the following method steps:
determining the second form of image data from the first form of the image data of the examination object;
determining a number of interfaces of the area of the body in the first form of the image data and in the second form of the image data;
determining a plurality of anatomical landmarks in the image data of the first form and in the image data of the second form;
determining a geometric curve in the first form of the image data and in the second form of the image data, wherein each of the curves run at least approximately in the interface and through the plurality of anatomical landmarks;
determining curve points in the geometric curves;
determining a plurality of contours in the interface of the first form of the image data and in the interface of the second form of the image data;
describing a geometric position of the target objects in the image data of the first form as a function of the contours of the first form of the image data; and
determining the geometric position of the target objects in the image data of the second form as a function of the contours of the second form of the image data, by interpolating between contours of the first form of the image data and contours of the second form of the image data.

17. The method according to claim 16, wherein the step of determining the second form of image data from the first form of the image data of the examination object comprises:
determining a set of a defined plurality of input pixels in the image data of the first form;
prognostically determining a set of target form parameters of a target form model with a defined plurality of target form parameters by way of a data-driven regression method from the plurality of input pixels, wherein the plurality of target form parameters is smaller than the plurality of input pixels; and
determining the second form of image data from the set of target form parameters.

18. A target object determination device in radiological imaging, for determining a geometric position of a number of target objects in a second form of image data from a geometric position of the target objects in a first form of image data of an area of a body of an examination object, the target object determination device comprising:
an interface configuration for receiving image data of the examination object in a first form and data concerning target objects in the first form of the image data and for receiving image data in a second form; and
the target object determination device being configured to carry out the following steps:
determining a number of interfaces of the area of the body in the first form of the image data and in the second form of the image data;
determining a plurality of anatomical landmarks in the image data of the first form and in the image data of the second form;
determining a geometric curve in the first form of the image data and in the second form of the image data, wherein the curves each run at least approximately in the interface and through the plurality of anatomical landmarks;
determining curve points in the geometric curves;
determining a plurality of contours in the interface of the first form of the image data and in the interface of the second form of the image data;
describing the geometric position of the target objects in the image data of the first form as a function of the contours of the first form of the image data; and
determining the geometric position of the target objects in the image data of the second form as a function of the contours of the second form of the image data, using interpolation between contours of the first form of the image data and contours of the second form of the image data.

19. An imaging device for radiological imaging, comprising one or both of an image processing workstation and a target object determination device, wherein:
 the image processing workstation is configured for determining a second form of image data from a first form of image data of an examination object and the image processing workstation comprises:
  an input pixel device configured for determining a set of a defined plurality of input pixels in the image data of the first form;
  a prognostic device configured for determining a set of target form parameters of a target form model with a defined plurality of target form parameters by way of a data-driven regression method from the plurality of input pixels, wherein the plurality of target form parameters is smaller than the plurality of input pixels; and
  an image data determination device configured for determining the second form of image data from the set of target form parameters; and
 said target object determination device is configured for determining a geometric position of a number of target objects in a second form of image data from a geometric position of the target objects in a first form of image data of an area of a body of an examination object and said target object determination device comprises:
  an interface configuration for receiving image data of the examination object in a first form and data concerning target objects in the first form of the image data and for receiving image data in a second form; and
  said target object determination device being configured to carry out the following steps:
   determining a number of interfaces of the area of the body in the first form of the image data and in the second form of the image data:
   determining a plurality of anatomical landmarks in the image data of the first form and in the image data of the second form;
   determining a geometric curve in the first form of the image data and in the second form of the image data, wherein the curves each run at least approximately in the interface and through the plurality of anatomical landmarks;
   determining curve points in the geometric curves;
   determining a plurality of contours in the interface of the first form of the image data and in the interface of the second form of the image data;
   describing the geometric position of the target objects in the image data of the first form as a function of the contours of the first form of the image data; and
   determining the geometric position of the target objects in the image data of the second form as a function of the contours of the second form of the image data, using interpolation between contours of the first form of the image data and contours of the second form of the image data.

20. A computer program product comprising program code stored in non-transitory form to be loaded into a memory of a programmable imaging device and/or an image processing workstation, the program code causing the execution of the method according to claim 1 when the program code is executed in the imaging device and/or the image processing workstation.

\* \* \* \* \*